United States Patent [19]
Yoon

[11] Patent Number: 5,645,557
[45] Date of Patent: *Jul. 8, 1997

[54] SAFETY PENETRATING INSTRUMENT WITH TRIGGERED PENETRATING MEMBER RETRACTION AND SAFETY MEMBER PROTRUSION

[76] Inventor: InBae Yoon, 2101 Highland Ridge Dr., Phoenix, Md. 21131

[*] Notice: The term of this patent shall not extend beyond the expiration date of Pat. No. 5,431,635.

[21] Appl. No.: 279,172

[22] Filed: Jul. 22, 1994

Related U.S. Application Data

[63] Continuation-in-part of Ser. No. 83,220, Jun. 24, 1993, Pat. No. 5,431,635, Ser. No. 83,728, Jun. 29, 1993, Pat. No. 5,466,224, Ser. No. 115,152, Sep. 2, 1993, Pat. No. 5,578,053, and Ser. No. 177,616, Jan. 4, 1994, said Ser. No. 83,220, and Ser. No. 83,728, each is a continuation-in-part of Ser. No.628,899, Dec. 18, 1990, Pat. No. 5,226,426, and Ser. No. 817,113, Jan. 6, 1992, Pat. No. 5,350,393.

[51] Int. Cl.$^6$ .................................................. A61M 5/00
[52] U.S. Cl. .......................... 606/185; 604/165; 604/170
[58] Field of Search ............................ 128/751, 752, 128/753, 754; 604/95, 158, 162, 163, 164, 165, 170, 272, 274, 280, 169; 606/167, 171, 185

[56] References Cited

U.S. PATENT DOCUMENTS

| | | |
|---|---|---|
| Re. 32,922 | 5/1989 | Levin et al. |
| 1,087,845 | 2/1914 | Stevens |
| 1,213,001 | 1/1917 | Philips |
| 1,248,492 | 12/1917 | Hill |
| 1,527,291 | 2/1925 | Zorraquin |
| 2,496,111 | 1/1950 | Turkel |
| 2,623,521 | 12/1952 | Shaw |
| 2,630,803 | 3/1953 | Baran |
| 4,254,762 | 3/1981 | Yoon |
| 4,345,589 | 8/1982 | Hiltebrandt |
| 4,442,836 | 4/1984 | Meinecke et al. |

(List continued on next page.)

FOREIGN PATENT DOCUMENTS

| | | |
|---|---|---|
| 2544262 | 4/1977 | Germany |
| 878265 | 11/1981 | U.S.S.R. |
| 897224 | 1/1982 | U.S.S.R. |
| 1435246 | 11/1988 | U.S.S.R. |
| 904635 | 8/1962 | United Kingdom |
| 9304632 | 3/1993 | WIPO |
| 9304715 | 3/1993 | WIPO |
| 9304716 | 3/1993 | WIPO |
| 9317626 | 9/1993 | WIPO |

*Primary Examiner*—Guy V. Tucker

[57] ABSTRACT

A safety penetrating instrument includes a penetrating member having a sharp distal end, a safety member movable relative to the penetrating member to protect the sharp distal end of the penetrating member, a safety member extending mechanism, a penetrating member retracting mechanism, a locking mechanism, a biasing mechanism and a releasing mechanism. The extending mechanism moves the safety member distally to a safety member extended position where the safety member distal end is disposed distally of the penetrating member distal end while permitting the safety member to move proximally to a safety member retracted position. The retracting mechanism moves the penetrating member proximally to a retracted position where the penetrating member distal end is disposed proximally of the safety member distal end while permitting the penetrating member to move distally to a penetrating member extended position. The locking mechanism locks the safety member in the safety member retracted position to prevent movement of the safety member to the safety member extended position and locks the penetrating member in the penetrating member extended position. The bias mechanism biases one or both of the safety member and penetrating member distally upon introduction in the anatomical cavity while permitting proximal movement of the members during penetration of the anatomical cavity wall. The releasing mechanism is responsive to distal movement of one or both of the safety member and penetrating member for triggering release of the locking mechanism.

37 Claims, 6 Drawing Sheets

U.S. PATENT DOCUMENTS

| | | |
|---|---|---|
| 4,488,545 | 12/1984 | Shen . |
| 4,503,856 | 3/1985 | Cornell et al. . |
| 4,535,773 | 8/1985 | Yoon . |
| 4,559,041 | 12/1985 | Razi . |
| 4,601,710 | 7/1986 | Moll . |
| 4,627,841 | 12/1986 | Dorr . |
| 4,654,030 | 3/1987 | Moll et al. . |
| 4,670,008 | 6/1987 | Von Albertini . |
| 4,677,979 | 7/1987 | Burns . |
| 4,747,831 | 5/1988 | Kulli . |
| 4,817,603 | 4/1989 | Turner et al. . |
| 4,820,275 | 4/1989 | Haber et al. . |
| 4,828,547 | 5/1989 | Sahi et al. . |
| 4,869,717 | 9/1989 | Adair . |
| 4,889,117 | 12/1989 | Stevens . |
| 4,900,307 | 2/1990 | Kulli . |
| 4,902,280 | 2/1990 | Lander . |
| 4,906,236 | 3/1990 | Alberts et al. . |
| 4,931,042 | 6/1990 | Holmes et al. . |
| 4,943,280 | 7/1990 | Lander . |
| 4,946,446 | 8/1990 | Vadher . |
| 4,955,870 | 9/1990 | Ridderheim . |
| 4,966,593 | 10/1990 | Lennox . |
| 4,973,316 | 11/1990 | Dysarz . |
| 4,994,042 | 2/1991 | Vadher . |
| 4,994,068 | 2/1991 | Hufnagle . |
| 5,024,665 | 6/1991 | Kaufman . |
| 5,026,388 | 6/1991 | Ingaiz . |
| 5,030,206 | 7/1991 | Lander . |
| 5,053,016 | 10/1991 | Lander . |
| 5,061,251 | 10/1991 | Juhasz . |
| 5,066,288 | 11/1991 | Deniega et al. . |
| 5,073,169 | 12/1991 | Raiken . |
| 5,104,382 | 4/1992 | Brinkerhoff et al. . |
| 5,104,383 | 4/1992 | Shichman . |
| 5,114,407 | 5/1992 | Burbank . |
| 5,116,353 | 5/1992 | Green . |
| 5,122,122 | 6/1992 | Allgood . |
| 5,127,909 | 7/1992 | Shichman . |
| 5,129,885 | 7/1992 | Green et al. . |
| 5,152,754 | 10/1992 | Plyley et al. . |
| 5,158,552 | 10/1992 | Borgia et al. . |
| 5,207,647 | 5/1993 | Phelps . |
| 5,215,526 | 6/1993 | Deniega et al. . |
| 5,224,951 | 7/1993 | Freitas . |
| 5,224,952 | 7/1993 | Deniega et al. . |
| 5,226,426 | 7/1993 | Yoon . |
| 5,226,891 | 7/1993 | Bushatz et al. . |
| 5,246,425 | 9/1993 | Hunsberger et al. . |
| 5,248,298 | 9/1993 | Bedi et al. . |
| 5,256,148 | 10/1993 | Smith et al. . |
| 5,256,149 | 10/1993 | Banik et al. . |
| 5,261,891 | 11/1993 | Brinkerhoff et al. . |
| 5,267,965 | 12/1993 | Deniega . |
| 5,275,583 | 1/1994 | Crainich . |
| 5,290,243 | 3/1994 | Chodorow et al. . |
| 5,290,304 | 3/1994 | Storace . |
| 5,295,993 | 3/1994 | Green . |
| 5,312,354 | 5/1994 | Allen et al. . |
| 5,318,580 | 6/1994 | Gresl . |
| 5,318,585 | 6/1994 | Guy et al. . |
| 5,320,610 | 6/1994 | Yoon . |
| 5,324,268 | 6/1994 | Yoon . |
| 5,330,432 | 7/1994 | Yoon . |
| 5,336,176 | 8/1994 | Yoon . |
| 5,338,305 | 8/1994 | Plyley et al. . |
| 5,346,459 | 9/1994 | Allen . |
| 5,350,393 | 9/1994 | Yoon . |
| 5,360,405 | 11/1994 | Yoon . |
| 5,364,372 | 11/1994 | Danks et al. . |
| 5,366,445 | 11/1994 | Haber et al. . |
| 5,368,607 | 11/1994 | Freitas . |
| 5,372,588 | 12/1994 | Farley et al. . |
| 5,374,252 | 12/1994 | Banks et al. . |
| 5,376,082 | 12/1994 | Phelps . |
| 5,380,288 | 1/1995 | Hart et al. . |
| 5,383,859 | 1/1995 | Sewell, Jr. . |

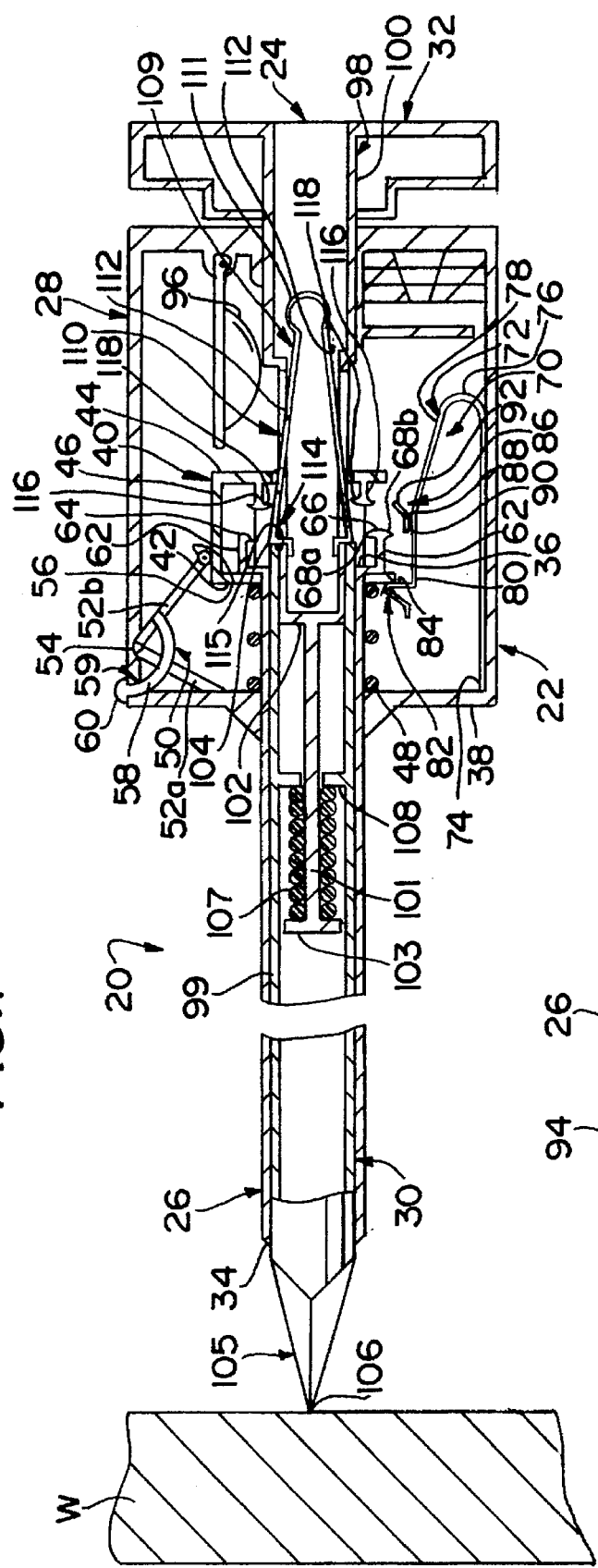

SAFETY PENETRATING INSTRUMENT WITH TRIGGERED PENETRATING MEMBER RETRACTION AND SAFETY MEMBER PROTRUSION

CROSS-REFERENCE TO RELATED APPLICATIONS

This application is a continuation-in-part of applications Ser. No. 08/083,220, filed Jun. 24, 1993, now U.S. Pat. No. 5,431,635 which is a continuation-in-part of prior applications Ser. No. 07/628,899 filed Dec. 18, 1990, now U.S. Pat. No. 5,226,426, and Ser. No. 07/817,113 filed Jan. 6, 1992, now U.S. Pat. No. 5,350,393; Ser. No. 08/083,728, filed Jun. 29, 1993, now U.S. Pat. No. 5,466,224, which is a continuation-in-part of prior applications Ser. No. 07/628, 899, filed Dec. 18, 1990, now U.S. Pat. No. 5,226,426, and Ser. No. 07/817,113, filed Jan. 6, 1992, now U.S. Pat. No. 5,350,393; Ser. No. 08/115,152, filed Sep. 2, 1993, now U.S. Pat. No. 5,578,053; and Ser. No. 08/177,616 filed Jan. 4, 1994, still pending, the disclosures of which are incorporated herein by reference.

BACKGROUND OF THE INVENTION

1. Field of the Invention

The present invention pertains to safety penetrating instruments and, more particularly, to safety penetrating instruments for use in forming portals for establishing communication with anatomical cavities wherein tissue and organ structures are protected from the tips of the penetrating members and to methods of penetrating anatomical cavity walls with safety penetrating instruments.

2. Discussion of the Prior Art

Penetrating instruments are widely used in medical procedures to gain access to anatomical cavities ranging in size from the abdomen to small blood vessels, such as veins and arteries, epidural, pleural and subarachnoid spaces, heart ventricles and spinal and synovial cavities. Use of penetrating instruments has become an extremely popular and important first step in endoscopic, or minimally invasive, surgery to establish an endoscopic portal for many various procedures, such as laparoscopic procedures in the abdominal cavity. Such penetrating instruments typically include a cannula or portal sleeve and a penetrating member disposed within the cannula and having a sharp tip for penetrating an anatomical cavity wall with the force required to penetrate the cavity wall being dependent upon the type and thickness of the tissue forming the cavity wall. Once the wall is penetrated, it is desirable to protect the sharp tip of the penetrating member from inadvertent contact with or injury to tissue or organ structures in or forming the cavity in that, once penetration is achieved, the lack of tissue resistance can result in the sharp tip traveling too far into the cavity and injuring adjacent tissue or organ structures.

Various safety penetrating instruments have been proposed, generally falling into protruding and retracting categories. In protruding safety penetrating instruments, a safety member is spring biased to protrude beyond the tip of the penetrating member in response to the reduced force on the distal end of the safety member upon entry into the anatomical cavity. The safety member can be disposed around the penetrating member in which case the safety member is frequently referred to as a shield, or the safety member can be disposed within the penetrating member in which case the safety member is frequently referred to as a probe. In retracting safety penetrating instruments, the penetrating member is retracted into the cannula upon entry into the anatomical cavity in response to distal movement of a component of the safety penetrating instrument such as the penetrating member, the cannula, a probe or a safety member such as a shield or probe.

While protruding safety penetrating instruments have been well received, there is room for improvement in reducing the force required to penetrate the cavity wall which necessarily includes the force required to overcome the spring bias on the safety member as well as the resistance of the cavity wall and insuring that the safety member protrudes which normally requires increasing the spring bias on the safety member and, thus, the force to penetrate. Retracting safety penetrating instruments have the disadvantages of requiring relatively complex mechanisms to hold the penetrating member in an extended position during penetration and to release the penetrating member for retraction and, concomitantly, not retracting sufficiently quickly and reliably.

SUMMARY OF THE INVENTION

Accordingly, it is a primary object of the present invention to overcome the above-mentioned disadvantages of the prior art and to provide a safety penetrating instrument responsive to movement of one or more members carried by the safety penetrating instrument during penetration of an anatomical cavity to trigger simultaneous retraction of the penetrating member and protrusion of the safety member to protect the tip of the penetrating member.

Another object of the present invention is to trigger simultaneous retraction of the penetrating member and protrusion of the safety member of a safety penetrating instrument in response to penetration of the safety penetrating instrument into an anatomical cavity.

Yet another object of the present invention is to bias the safety member of a safety penetrating instrument to move distally upon penetration into an anatomical cavity to trigger release of the penetrating member to move proximally to a retracted position and release of the safety member to move further distally to an extended protruding position protecting the tip of the penetrating member.

A further object of the present invention is to bias the penetrating member of a safety penetrating instrument to move distally upon penetration into an anatomical cavity to trigger release of the penetrating member to move proximally to a retracted position and release of the safety member to move distally to an extended protruding position protecting the tip of the penetrating member.

Yet a further object of the present invention is to bias the penetrating member and safety member of a safety penetrating instrument to move distally upon penetrating into an anatomical cavity to trigger release of the penetrating member to move proximally to a retracted position and release of the safety member to move further distally to an extended protruding position protecting the tip of the penetrating member.

An additional object of the present invention is to move an operating member of a safety penetrating instrument proximally a predetermined distance during penetration of an anatomical cavity wall to trigger release of the safety member to move distally to an extended protruding position and release of the penetrating member to move proximally to a retracted position.

The present invention has as an additional object to increase the distal force biasing the safety member in a safety penetrating instrument to assure protrusion of the safety member upon penetration into an anatomical cavity while minimizing the force-to-penetrate required.

A still further object of the present invention is to independently trigger retraction of a proximally biased penetrating member and protrusion of a distally biased safety member in a safety penetrating instrument upon penetration of the safety penetrating instrument into an anatomical cavity.

Yet another object of the present invention is to bias the safety member of a safety penetrating instrument distally to an extended position and to lock the safety member in a safety member retracted position preventing movement of the safety member to the safety member extended position while allowing the safety member to move proximally from the safety member retracted position during penetration of an anatomical cavity wall and distally toward the safety member retracted position upon introduction in the anatomical cavity to trigger further distal movement of the safety member to the safety member extended position, proximal movement of a penetrating member to a penetrating member retracted position, or both.

It is an additional object of the present invention to bias a penetrating member of a safety penetrating instrument proximally to a retracted position and to lock the penetrating member in a penetrating member extended position preventing movement of the penetrating member to the penetrating member retracted position while allowing the penetrating member to move proximally from the penetrating member extended position during penetration of an anatomical cavity wall and distally toward the penetrating member extended position upon introduction into the anatomical cavity to trigger distal movement of the safety member to the safety member extended position, proximal movement of the penetrating member to the penetrating member retracted position, or both.

Still another object of the present invention is to bias the safety member of a safety penetrating instrument distally to an extended position and the penetrating member of the safety penetrating instrument proximally to a retracted position, to lock the safety member in a safety member retracted position preventing movement of the safety member to the safety member extended position while allowing the safety member to move proximally a predetermined distance, to lock the penetrating member in a penetrating member extended position preventing movement of the penetrating member to the penetrating member retracted position while allowing the penetrating member to move proximally a predetermined distance, and to trigger further distal movement of the safety member to the safety member extended position and proximal movement of the penetrating member to the penetrating member retracted position in response to movement of one or both of the penetrating member and safety member upon penetrating into an anatomical cavity.

Some of the advantages of the present invention over the prior art are that the distal bias force on the safety member can be designed to assure protrusion of the safety member regardless of the anatomical tissue being penetrated, that penetration of an anatomical cavity wall by the safety penetrating instrument can be commenced with the safety member in a retracted position exposing the tip of the penetrating member, that the distal bias to move the safety member into an extended position is not required to be overcome during penetration of the anatomical cavity wall, that retraction of the penetrating member and protrusion of the safety member can be achieved with a single trigger mechanism or with separate independent trigger mechanisms for varying degrees of redundant safety, that the safety and efficacy of safety penetrating instruments can be enhanced since two modes of safety are provided, that in some instances the overall length of the safety penetrating instrument can be reduced by incorporating retracting and extending mechanisms within the housing, the penetrating member, the hub or combinations thereof, and that the safety penetrating instrument of the present invention can be inexpensively manufactured with minimum components to reduce cost, facilitate sterilization for reuse and allow economical, single-patient use.

The present invention is generally characterized in a safety penetrating instrument including a penetrating member and a safety member, such as a portal sleeve or cannula. The penetrating member is movable relative to the safety member from a penetrating member extended position where a sharp distal end of the penetrating member protrudes beyond a distal end of the safety member to a penetrating member retracted position where the penetrating member distal end is disposed proximally of the safety member distal end. The safety member is movable relative to the penetrating member between a safety member extended position where a distal end of the safety member protrudes distally of the penetrating member distal end and a safety member retracted position where the safety member distal end is disposed proximally of the penetrating member distal end with the penetrating member in the penetrating member extended position. The safety member is biased distally in the safety member retracted position to permit movement of the safety member proximally from the safety member retracted position during penetration of an anatomical cavity wall and distally toward the safety member retracted position upon introduction of the safety penetrating instrument into an anatomical cavity. A penetrating member locking means for locking the penetrating member in the penetrating member extended position during penetration of the anatomical wall is released in response to distal movement of either or both the safety member and penetrating member to permit a retracting means to move the penetrating member to the penetrating member retracted position. A safety member locking means for preventing movement of the safety member to the safety member extended position during penetration of the anatomical wall is released in response to distal movement of either or both the safety member and penetrating member to permit a safety member bias means to move the safety member further distally to the safety member extended position thusly providing two modes of safety, i.e. retraction of the penetrating member and protrusion of the safety member. The safety penetrating instrument according to the present invention can be provided with a single trigger mechanism or separate, independent trigger mechanisms for triggering retraction of the penetrating member and protrusion of the safety member, respectively.

Another aspect of the present invention is generally characterized in a method of forming a portal in the wall of an anatomical cavity by penetrating the anatomical cavity wall with a penetrating member of a safety penetrating instrument having a protective state where the penetrating member is moved proximally to a retracted position and a safety member is moved distally to an extended position to protect the distal end of the penetrating member, and triggering the safety penetrating instrument to move to the protective state when the safety penetrating instrument enters the anatomical cavity. Movement of the penetrating member to the penetrating member retracted position and the safety member to the safety member extended position is triggered by entry of one or both members into the anatomical cavity.

Other objects and advantages of the present invention will become apparent from the following description of the preferred embodiments taken in conjunction with the accompanying drawings wherein, unless specified otherwise, like parts or parts that perform like functions are identified in each of the several figures by the same reference character or by reference characters sharing the same last two digits.

BRIEF DESCRIPTION OF THE DRAWINGS

FIG. 1 is a broken side view, partly in section, of a safety penetrating instrument according to the present invention.

FIG. 2 is a broken side view, partly in section, of a distal end of the safety penetrating instrument of FIG. 1.

DESCRIPTION OF THE PREFERRED EMBODIMENTS

Figure 3:
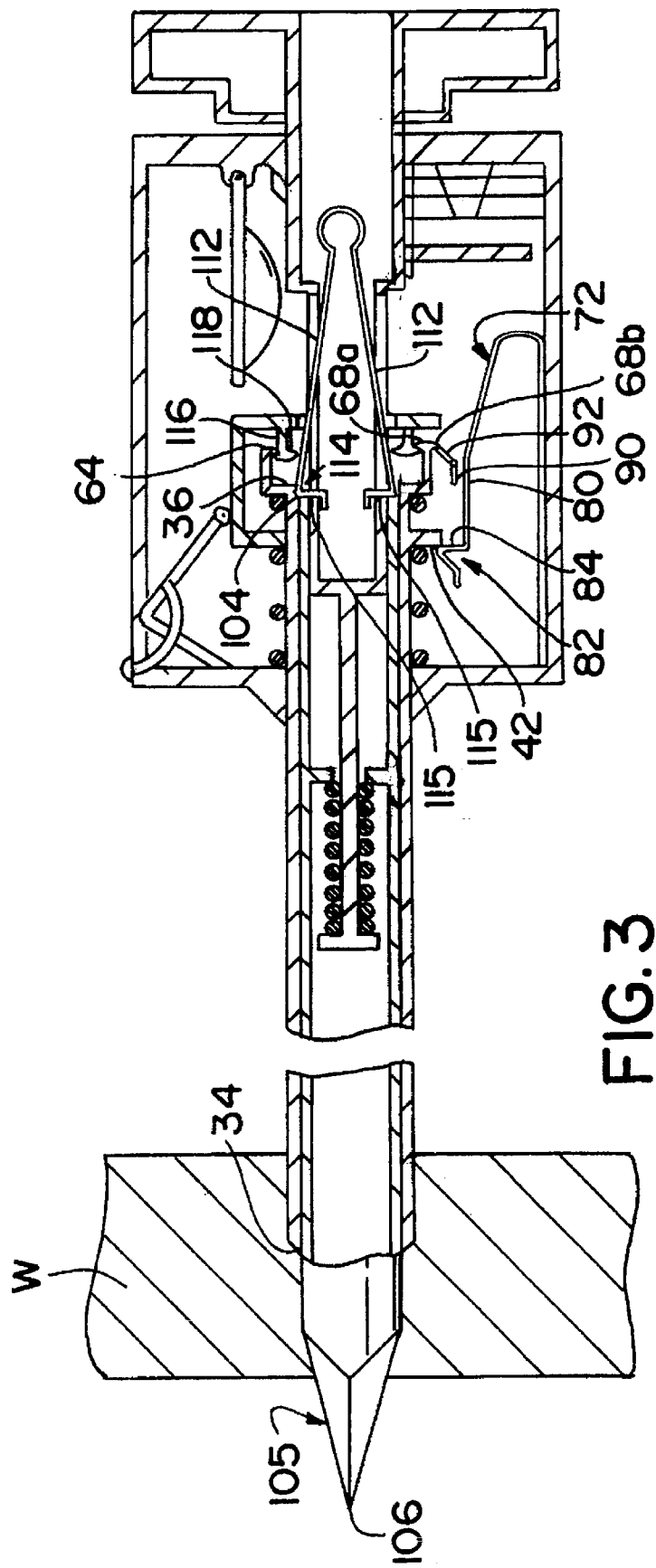
FIG. 3 is a broken side view, partly in section, of the safety penetrating instrument of FIG. 1 during penetration of an anatomical cavity wall.

The safety penetrating instrument of the present invention is described hereinafter for use as an instrument for inserting a portal sleeve through a wall of an anatomical cavity to form a portal for the introduction of various surgical and diagnostic instruments into the cavity during endoscopic procedures, such as laparoscopy. It is understood, however, that the safety penetrating instrument of the present invention can be used for safe penetration or introduction into anatomical cavities of needles with fluid flow therethrough and catheters as well as for other instruments engaging tissue during surgical or diagnostic procedures. Accordingly, the cannula or outer tubular member of the safety penetrating instrument can be a portal sleeve, a needle, a catheter or a tubular component of a medical instrument.

A safety penetrating instrument 20 according to the present invention, as shown in FIG. 1, is formed of a portal unit 22 and a penetrating unit 24. The portal unit 22 includes an elongate portal sleeve, cannula or catheter 26 and a housing 28 mounting a proximal end of portal sleeve 26. The penetrating unit 24 includes an elongate penetrating member 30 disposed in portal sleeve 26 and a hub 32 mounting a proximal end of the penetrating member. The hub 32 can be latched to the housing 28 with the use of any suitable releasable mechanism, such as detents operated by buttons, allowing the hub to be removed from the housing withdrawing the penetrating member from the portal sleeve.

The portal unit 22 can be made of any desirable, medical grade materials depending on procedural use and desirability of being for single patient use or reusable. Portal sleeve 26 can be cylindrical, tubular or have any other desired configuration in cross-section in accordance with the procedure to be performed and the anatomical cavity to be penetrated. Portal sleeve 26 is preferably made of a substantially cylindrical length of rigid or flexible and transparent or opaque material, such as stainless steel or other medically acceptable plastic or metal material, and defines a lumen for receiving penetrating member 30. Portal sleeve 26, which serves as a safety member, terminates distally at a distal end 34 and proximally at a transverse flange 36 disposed in housing 28 with the portal sleeve passing through an opening in a front wall 38 of the housing.

A rail member 40 is disposed in housing 28 and is generally U-shaped in configuration including a forward wall 42 disposed transverse or perpendicular to a longitudinal axis of the safety penetrating instrument 20, a rearward wall 44 parallel to forward wall 42 and a side wall 46 transversely joining the rail member forward and rearward walls. Flange 36 is disposed between the rail member forward and rearward walls 42 and 44, with rail member forward wall 42 having an opening therein allowing passage therethrough by the portal sleeve 26. The rail member forward and rearward walls 42 and 44 are disposed parallel or substantially parallel to flange 36, and a bias member 48 is connected between flange 36 and front wall 38 of housing 28 to bias the portal sleeve 26 distally with flange 36 in abutment with rail member forward wall 42. Bias member 48 includes a helical coil spring 48 disposed around portal sleeve 26 and mounted in tension between housing wall 38 and flange 36 with the opening in the rail member forward wall 42 being larger than the outer diameter or size of the portal sleeve to allow passage therethrough by the bias member 48. Although a helical coil spring is shown as the bias member 48 in FIG. 1, the bias member 48 can include various types of springs or other bias devices including tension springs, compression springs, torsion springs, pan springs, rubber, plastic or magnets, for example.

An extending member 50 is connected between the housing front wall 38 and the rail member 40 to bias the portal sleeve distally to a portal sleeve or safety member extended position. Extending member 50 can include various tension springs, compression springs, pan springs, torsion springs, rubber, plastic or magnets, for example, or any other type of bias device. As shown in FIG. 1, extending member 50 is made up of legs 52a and 52b flexibly or pivotally connected to one another at a flexible joint, hinge or pivot 54. Leg 52a is connected between housing front wall 38 and pivot 54 disposed along an upper wall of the housing, and leg 52b is connected between pivot 54 and a flexible joint, hinge or pivot 56 along the rail member 40, the pivot 56 being disposed along the rail member side wall 46. A torsion spring (not shown) is disposed around pivot 54 and connected between housing 28 and leg 52b to bias leg 52b distally toward leg 52a and, therefore, portal sleeve 26 to the portal sleeve extended position. A curved leg segment 58 extends from leg 52b through a slot, aperture or opening 59 in the upper wall of the housing and terminates at a knob, button or handle 60. The curved leg segment 58 is movable in and out of the housing via the handle 60 to pivot leg 52b to move rail member 40 as described further below.

A pair of opposed fingers 62 extend proximally from flange 36 in a perpendicular or transverse direction with one of the fingers terminating at a barb 64, and the other of the fingers terminating at a prong 66. Fingers 62 are disposed on opposite sides of the penetrating member parallel or substantially parallel with the instrument longitudinal axis. Barb 64 is angled distally from the one finger 62 in the direction of the instrument longitudinal axis. Prong 66 has a hook-like configuration with a barb 68a angled distally from the other finger 62 in the direction of the instrument longitudinal axis and an opposing prong 68b angled distally from the other finger 62 in a direction outwardly or away from the instrument longitudinal axis.

A locking and releasing mechanism 70 for locking the portal sleeve 26 in a portal sleeve or safety member retracted position exposing a sharp distal end of the penetrating member and for releasing the portal sleeve to move to the portal sleeve extended position includes a latch or locking spring 72, made of a strip of resilient material, formed to have a substantially flat base 74 secured to a lower wall of housing 28 and a bend 76 joining the base 74 with an upwardly angled arm 78 spaced from the base. Arm 78 has a distal extension 80 disposed parallel or substantially parallel with the longitudinal axis of the safety penetrating instrument and carries or forms a protruding latch 82. As shown in FIG. 1 latch 82 is disposed distally of arm extension 80 and includes a proximal angled latching surface 84 disposed substantially transverse to the longitudinal axis of the safety penetrating instrument and substantially parallel to the rail member forward wall 42. A releasing member or trigger 86 is juxtaposed with arm extension 80 and is pivotally mounted in the housing on a pin 88 secured to a wall or walls of the housing or structure supported in the housing. Trigger 86 is generally L-shaped with a leg 90 overlying extension 80 and a leg 92 extending substantially transverse from leg 90 but at a slight angle toward the proximal end of the safety penetrating instrument. A torsion spring (not shown) is coiled around pin 88 and fixed to trigger 86 to bias the trigger counterclockwise, looking at FIG. 1, such that leg 90 is biased toward extension 80.

The portal sleeve or safety member distal end 34 can have various configurations to protect tissue within an anatomical cavity by covering the distal tip of the penetrating member with the portal sleeve in the portal sleeve extended position; and, as shown, the portal sleeve distal end defines an annular or peripheral edge having a relatively blunt or chamfered configuration to ease penetration while protecting tissue within the anatomical cavity. The portal sleeve can be provided with a shape or surface texture to increase resistance of the portal sleeve to passage through anatomical tissue such that the portal sleeve moves proximally against the bias of spring 48 during penetration of anatomical tissue by the safety penetrating instrument. The resistance of the portal sleeve can be increased in many various ways such as by roughening, texturing or dimpling the external surface of the portal sleeve or by providing the external surface with bumps, threads, ridges or other irregularities or by configuring the portal sleeve to have a slight enlargement or protrusion. As illustrated in FIG. 2, the external surface of the portal sleeve 26 can be ribbed or grooved and slightly enlarged along a distal segment 94 adjacent the portal sleeve distal end 34 to increase the resistance of the portal sleeve to penetration or passage through anatomical tissue. Movement of the portal sleeve against the bias member 48 can also be assured by selecting the strength of the bias member to cause proximal movement of the portal sleeve during penetration of anatomical tissue due to a force from tissue contact at a distal end of the portal sleeve such that the shape or external surface of the portal sleeve need not be modified and can be conventional.

The housing 28 can be made of any desirable material and can have any desirable configuration to facilitate grasping by a surgeon and includes a rear wall having an opening therein aligned with the opening in housing front wall 38 to allow passage therethrough by the penetrating member 30. The housing 28 is preferably constructed to sealingly engage instruments passing therethrough and to include a valve 96 biased to a closed state when no instrument passes through the portal sleeve. A flapper valve 96 is shown; however, any suitable valve construction can be utilized, for example trumpet or nipple valves.

Penetrating member 30 is made up of an inner or end part 98 and an outer or distal part 99 mounted for telescoping sliding movement relative to end part 98. End part 98 includes a tubular or hollow or partly tubular or hollow rearward section 100 and a forward section 101 having a periphery, circumference or cross-section smaller than a periphery, circumference or cross-section of rearward section 100. Rearward section 100 terminates proximally at a proximal end of the penetrating member secured to hub 32 and distally at a transverse stop or end wall 102. Forward section 101 extends distally from end wall 102 to terminate at a transverse flange 103 disposed in distal part 99. Distal part 99 is hollow or tubular or partly hollow or tubular to receive forward section 101 and a portion of rearward section 100, and has an inner diameter or size to closely receive the rearward section. Distal part 99 terminates proximally at an edge 104 disposed in housing 28 and distally at a distal end 105 having a sharp tip or point 106 for penetrating anatomical tissue. The distal end 105 can have any configuration desired by a surgeon for a particular procedure, for example, the pyramidal trocar configuration shown or conical, threaded, multifaceted or open, slanted, hollow or tubular needle configurations. The penetrating member 30 can be made of any suitable, medical grade materials and can be made of multiple components such that, for example, the distal end 105 can be made of stainless steel and secured in any conventional manner, such as by threads, to a shaft or body of the penetrating member, which can be tubular and made of a less expensive material, such as plastic or metal. A retracting member 107 biases the distal part 99 proximally relative to the end part 98 and includes a helical coil retracting spring 107 disposed around forward section 101 and mounted in compression between flange 103 and an internal wall or shoulder 108 of distal part 99 to bias the distal part proximally relative to end part 98 to a penetrating member retracted position where sharp tip 106 is disposed proximally of portal sleeve distal end 34. Although a helical coil spring is illustrated in FIG. 1 as the retracting member, it will be appreciated that the retracting member can include various other types of springs as well as various other types of bias devices other than springs as discussed above for bias member 48 and extending member 50. A plate, pin or flange, such as pin 145 of FIG. 5, can be coupled with distal part 99 to extend through a slot, such as slot 147 shown in FIG. 5, in housing 28 with the plate or flange terminating at a knob or handle, such as handle 149 shown in FIG. 5, movable along the slot for moving the distal part 99 relative to the end part 98 to move the penetrating member to the penetrating member extended position.

A locking and releasing mechanism 109 for locking the penetrating member 30 in a penetrating member extended position where sharp tip 106 protrudes beyond portal sleeve distal end 34 with the portal sleeve in the portal sleeve retracted position and for releasing the penetrating member to move to the penetrating member retracted position includes a latch or locking spring 110 mounted in rearward section 100. Locking spring 110 is made of a strip of resilient material formed to have a partial or semi-circular base 111 secured to or supported by a wall of rearward section 100 or to structure supported in rearward section 100 and a pair of opposed arms 112 angled outwardly from opposing ends of base 111 in a direction away from the longitudinal axis of the safety penetrating instrument to extend distally to protrude through opposed slots 113 in rearward section 100. Arms 112 carry or form latches 114 having distal angled latching surfaces 115 extending inwardly from arms 112 in the direction of the longitudinal axis to be disposed substantially transverse to the longitudinal axis. Releasing or trigger members are juxtaposed with arms 112 and include legs 116 flexibly, resiliently or pivotally connected to rail member rearward wall 44 to extend distally therefrom in a transverse or perpendicular direction to terminate at enlarged nubs 118 disposed in the path of longitudinal movement of barb 64 and barb 68a when flange 36 is moved longitudinally.

Hub 32 can be made of any desirable medical grade material and can have any desired configuration in cross-section to facilitate grasping of the hub and the housing by a surgeon with one hand.

Figure 4:
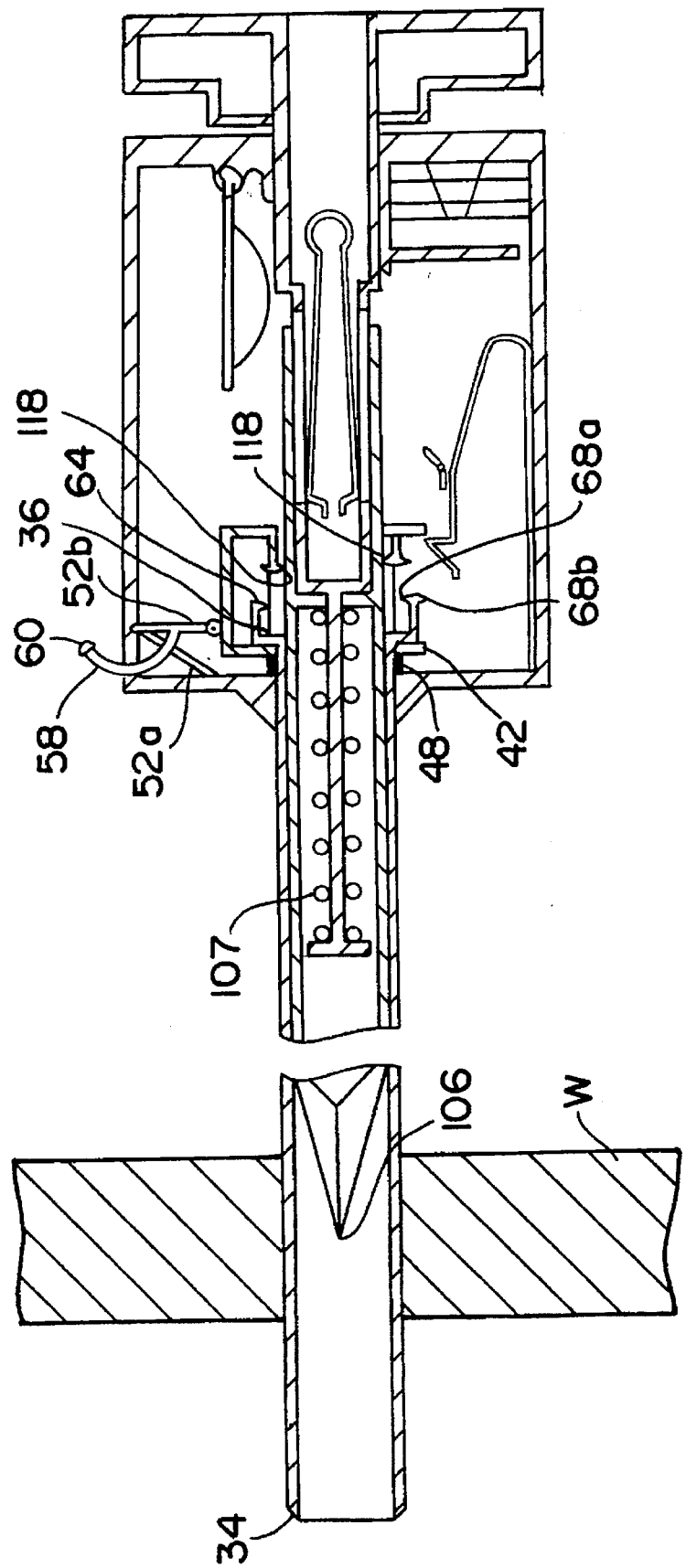
FIG. 4 is a broken side view, partly in section, of the safety penetrating instrument of FIG. 1 following introduction of the safety penetrating instrument in the anatomical cavity.
Figure 5:
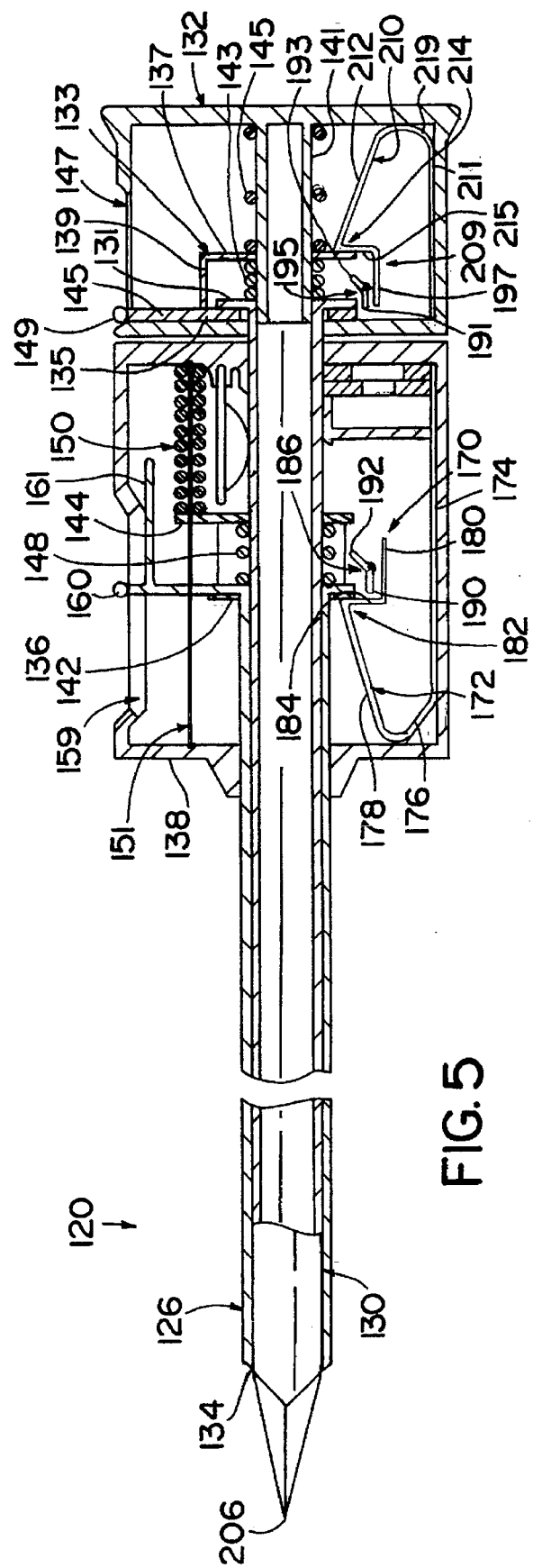
FIG. 5 is a broken side view, partly in section, of another embodiment of a safety penetrating instrument according to the present invention.

In use, the safety penetrating instrument 20 can be provided in the condition illustrated in FIG. 4 with the penetrating member 30 in the penetrating member retracted position where the sharp tip 106 of the penetrating member is disposed proximally of the distal end 36 of the portal sleeve and with the portal sleeve 26 in the portal sleeve extended position. The safety penetrating instrument 20 can also be provided with the penetrating member 30 in the penetrating member retracted position and with the portal sleeve 26 in the portal sleeve retracted position at which time the sharp tip 106 of the penetrating member will still be disposed proximally of the distal end 36 of the portal sleeve, the portal sleeve being shown in the portal sleeve retracted position in FIG. 1.

Where the instrument 20 is provided with the portal sleeve 26 in the portal sleeve extended position and with the penetrating member 30 in the penetrating member retracted position as shown in FIG. 4, prior to commencing penetration of an anatomical wall W, button 60 is pressed causing curved segment 58 to be moved further into the housing 28. Movement of the curved segment 58 into the housing 28 causes leg 52b to be moved by the curved segment 58 proximally away from leg 52a, the leg 52b pivoting around pivot 54. Movement of leg 52b away from leg 52a causes rail member 40 to be moved longitudinally in a proximal direction, carrying with it portal sleeve 26, until rail member forward wall 42 rides over latch 82. Movement of rail member forward wall 42 proximally past latch 82 causes locking spring 72 to spring back to its normal position illustrated in FIG. 1 at which time the rail member forward wall 42 will be held against latching surface 84 to lock the portal sleeve in the portal sleeve retraced position where movement of the portal sleeve to the portal sleeve extended position is prevented. With the portal sleeve in the portal sleeve retracted position, flange 36 will be biased distally by bias member 48 to abut rail member forward wall 42 with barb 68b of prong 66 disposed distally of trigger leg 92. Prior to commencing penetration of the anatomical wall W, the penetrating member 30 is moved to the penetrating member extended position by grasping the handle, such as handle 149 of FIG. 5, coupled with distal part 99 and manually moving the handle along the slot, such as slot 147, in housing 28 to move the distal part 99 distally relative to the edge part 98 until end 104 is moved distally past latches 114 to uncover slots 113 in rearward section 100. Although handle 149 is illustrated in FIG. 5 as being movable along slot 147 disposed in an upper wall of hub 132, it will be appreciated that the handle and slot can be arranged in many various ways in the hub or the housing in accordance with the arrangement of the locking and releasing mechanisms therein and that, for example, the slot 147 can be provided in a side wall of housing 28 of the safety penetrating instrument 20 with the handle 149 coupled with distal part 99 to extend through the slot 147. Movement of edge 104 distally past latches 114 to uncover slots 113 causes arms 112 to spring back to the normal position for locking spring 110 illustrated in FIG. 1 with the arms 112 protruding through the slots 113 to engage edge 104. With edge 104 engaged by latching surfaces 115, the penetrating member 30 will be locked in the penetrating member extended position with sharp tip 106 disposed distally of portal sleeve distal end 34 and barbs 64 and 68a disposed distally of nubs 118.

During penetration of the anatomical wall W, a force from tissue contact due to resistance of the anatomical tissue will cause the portal sleeve 26 to move proximally from the portal sleeve retracted position against the distal bias of bias member 48 causing the operating member formed by flange 36, barb 64 and prong 66 to move proximally. Barbs 64 and 68a will be moved proximally past nubs 118 without causing movement of latches 114 out of engagement with edge 104 such that the penetrating member remains locked in the penetrating member extended position. Movement of prong 66 proximally causes barb 68b to be moved proximally past trigger leg 92 without causing movement of latch 82 out of engagement with rail member forward wall 42 such that the portal sleeve is still locked against movement to the portal sleeve extended position. Accordingly, during penetration of the anatomical wall W, the distal bias of the extending member 50 biasing the portal sleeve to the portal sleeve extended position need not be overcome.

Upon introduction of the portal sleeve distal end 34 in the anatomical cavity, a decrease, reduction or removal of the force from anatomical tissue causes the portal sleeve 26 to move distally toward the portal sleeve retracted position. Movement of portal sleeve 26 distally toward the portal sleeve retracted position, causes longitudinal distal movement of the operating member such that barbs 64 and 68a engage nubs 118 to cam or pivot trigger legs 116 inwardly in the direction of the instrument longitudinal axis as shown in FIG. 3. Movement of trigger legs 116 toward the instrument longitudinal axis causes arms 112 to be moved inwardly toward the instrument longitudinal axis to move latches 114 out of engagement with edge 104. Movement of latches 114 out of engagement with edge 104 causes the retracting member 107 to move the distal part 99 proximally relative to the end part 98 to move the penetrating member 30 to the penetrating member retracted position where sharp tip 106 is disposed proximally of the distal end 34 of the portal sleeve. Movement of flange 36 distally toward the portal sleeve retracted position also causes barb 68b of prong 66 to engage trigger leg 92 to pivot the trigger 86 counterclockwise looking at FIG. 3. Pivoting of trigger 86 causes trigger leg 90 to engage arm extension 80 to move arm 78 toward base 74 against the force of the spring strip 72. Movement of arm 78 in a direction away from the instrument longitudinal axis causes latch 82 to move out of engagement with rail member forward wall 42 thereby allowing extending member 50 to move the portal sleeve further distally to the portal sleeve extended position. Accordingly, upon introduction of the safety penetrating instrument in the anatomical cavity, the portal sleeve 26 will be in the portal sleeve extended position and the penetrating member 30 will be in the penetrating member retracted position. The penetrating unit 24 can then be withdrawn from the portal unit 22 leaving the portal sleeve in place in the anatomical cavity.

With the safety penetrating instrument 20, two modes of safety are provided, i.e. retraction of the penetrating member and protrusion of the portal sleeve, which serves as a safety member, and the bias force assuring protrusion of the safety member does not have to be overcome during penetration. Although the portal sleeve is disclosed herein as the safety member, it will be appreciated that the safety member can be any other member including a shield or probe. The bias force for biasing the safety member to the safety member extended position can be relatively strong to assure protrusion of the safety member even should the safety member engage tissue in the anatomical cavity wall or within the anatomical cavity or should any tissue be jammed between the safety member and the penetrating member and/or the portal sleeve. The strong distal bias toward the safety member extended position provides the surgeon with the psychological benefit of knowing the safety member is protecting the penetrating member and provides an easily felt tactile signal that the safety member has moved to the safety member extended position for confirmation of penetration. Movement of the safety member to the safety member extended position can also be confirmed visually by noticing movement of the curved segment 58 out of housing 28. Should tissue within the anatomical cavity be contacted by the distal end of the safety member, the safety member can bounce or give a little in the nature of a shock absorber to protect such contacted tissue. The safety member can have various configurations so long as the distal end of the safety member protrudes beyond the sharp tip of the penetrating member to provide a protective function, and a plurality of safety members can be employed in the safety penetrating instrument. By providing two modes of safety, one relying on protrusion of the safety member and the other relying on retraction of the penetrating member, protection of the sharp tip of the penetrating member upon penetration into the anatomical cavity can be ensured even should one of the safety modes malfunction during use. The bias force for biasing the safety member distally when the safety member is in the safety member retracted position need only be great enough to produce slight longitudinal movement of the operating member during penetration.

Another embodiment of a safety penetrating instrument according to the present invention is illustrated at 120 in FIG. 5. The safety penetrating instrument 120 is similar to safety penetrating instrument 20 in that retraction of the penetrating member and protrusion of the safety member are provided; however, the instrument 120 is different in that separate, independent trigger mechanisms are provided for releasing the safety member to move to the safety member extended position and for releasing the penetrating member to move to the penetrating member retracted position. Portal unit 122 for safety penetrating instrument 120 is similar to portal unit 22 and includes portal sleeve 126 terminating proximally at flange 136 disposed between a forward wall 142 and a rearward wall 144 of rail member 140. Flange 136 extends through a slot 159 in an upper wall of housing 128 to terminate at a knob or handle 160. Slot 159 extends longitudinally parallel with a longitudinal axis of the safety penetrating instrument 120, and an indicator strip 161 extends proximally from flange 136 in a transverse or perpendicular direction to be visible along the slot 159. Indicator strip 161 can be colored and/or provided with any suitable indicia to be visible along the slot 159 to provide an indication to the surgeon of the position of the portal sleeve 126 as will be explained further below. A bias member 148, including a helical coil spring disposed around penetrating member 130 and mounted in compression between flange 136 and a rear wall 144 of rail member 140, biases the portal sleeve distally such that flange 136 is in abutment with rail member forward wall 142. An extending member 150 including a helical coil spring is connected between rail member rearward wall 140 and a rear wall of housing 128 to bias the portal sleeve to the portal sleeve extended position. If desired, a guide rod 151 can be connected between the housing front wall 138 and the housing rear wall to pass through flange 136 and rail member 144 with the spring 150 being disposed around the guide rod.

Locking and releasing mechanism 170 for locking the portal sleeve in the portal sleeve retracted position where movement of the portal sleeve to the portal sleeve extended position is prevented and for releasing the portal sleeve to allow the portal sleeve to move to the portal sleeve extended position is similar to locking and releasing mechanism 70 and includes a latch or locking spring 172 having a substantially flat base 174 secured to a lower wall of housing 128 and a bend 176 joining the base 174 with an upwardly angled arm 178. Arm 178 has a proximal arm extension 180 disposed parallel or substantially parallel with the longitudinal axis of the safety penetrating instrument 120 and carries or forms a latch 182 having a proximal angled latching surface 184 disposed substantially transverse to the longitudinal axis of the safety penetrating instrument and substantially parallel to the rail member forward wall 142. A releasing member or trigger 186 is juxtaposed with arm extension 180 and is similar to trigger 86.

Penetrating member 130 for safety penetrating instrument 120 terminates proximally at a transverse flange 131 disposed in hub 132 with the penetrating member passing through aligned openings in the rail member forward and rearward walls 142 and 144 and in the rear wall of housing 128. A rail member 133 is disposed in hub 132 and has a generally U-shaped configuration with spaced, parallel forward and rearward walls 135 and 137, respectively, and a side wall 139 connecting the rail member forward and rearward walls 135 and 137. Flange 131 is disposed between the rail member forward and reward walls 135 and 137 with the penetrating member passing through aligned openings in a forward wall of hub 132 and rail member forward wall 135. A control or guide tube or shaft 141 extends distally from a rear wall of hub 132 into a proximal end of penetrating member 130 with the guide shaft extending through an opening in the rail member rearward wall 137.

A bias member 143 is connected between flange 131 and the rail member rearward wall 137 to bias the penetrating member in a distal direction such that flange 131 is biased in abutment with rail member forward wall 135. Bias member 143 is shown as a helical coil spring disposed around guide shaft 141; however, bias member 143 can include any other type of spring or other bias device as previously discussed for bias member 48 and extending member 50. A retracting member 145 is mounted around guide tube 141 and connected between the rail member rearward wall 137 and a rear wall of hub 132 to bias the rail member 133 and, therefore, the penetrating member 130, proximally to the penetrating member retracted position. A pin or flange 145 extends from rail member 133 and trough a slot 147 in an upper wall of hub 132 to terminate at a knob or handle 149. Slot 147 is disposed parallel with the instrument axis with the handle 149 being movable along the slot 147 for use in moving the penetrating member 130 to the penetrating member extended position as explained further below.

A locking and releasing mechanism 209 for locking the penetrating member 130 in the penetrating member extended position and for releasing the penetrating member to move to the penetrating member retracted position includes a latch or locking spring 210, made of a strip of resilient material, formed to have a substantially flat base 211 secured to a lower wall of hub 132 and a bend 219 joining the base 211 to an upwardly angled arm 212. Arm 212 carries or forms a latch 214 having a distal angled latching surface 215 and a distal arm extension 197 disposed distally of latch 214. A releasing or trigger member 195 is juxtaposed with arm extension 197 and is similar to trigger member 195. Trigger member 195 is generally L-shaped including a trigger leg 191 overlying extension 197 and a leg 193 extending substantially transverse from leg 191 but at a slight angle toward the proximal end of the safety penetrating instrument.

Operation of safety penetrating instrument 120 is similar to that previously described in that the instrument 120 can be provided with the portal sleeve 126 in either the portal sleeve retracted position or the portal sleeve extended position and with the penetrating member 130 in the penetrating member retracted position where sharp tip 206 is disposed proximally of a distal end 134 of the portal sleeve. Where the instrument 120 is provided with the portal sleeve 126 in the portal sleeve extended position, prior to penetration of an anatomical wall, handle 160 is grasped and manually moved proximally along slot 159 to move the portal sleeve to the portal sleeve retracted position with rail member forward wall 142 in engagement with latching surface 184 at which time the portal sleeve will be in the portal sleeve retracted position and will be prevented from moving to the portal sleeve extended position. With the portal sleeve in the portal sleeve retracted position, flange 136 will be biased in abutment with rail member forward wall 142 and will be disposed distally of trigger leg 192.

The penetrating member 130 is then moved to the penetrating member extended position by moving the handle 149 distally along the slot 147 until rail member 133 rides past latch 214. Movement of rail member 133 distally past latch 214 causes locking spring 210 to spring back to its normal position illustrated in FIG. 5 such that latching surface 215 engages the rail member rearward wall 137 at which time the penetrating member will be locked in the penetrating member extended position. With the penetrating member 130 in the penetrating member extended position, the penetrating member 130 will be biased distally with flange 131 biased to abut rail member forward wall 135 and with flange 131 disposed distally of trigger leg 191. The instrument will then be in the condition shown in FIG. 5 with the portal sleeve in the portal sleeve retracted position and the penetrating member in the penetrating member extended position with sharp tip 206 disposed distally of portal sleeve distal end 134.

During penetration of an anatomical cavity wall, the force from tissue contact due to resistance of the anatomical wall will cause penetrating member 130 to be moved proximally against the bias of bias member 143 causing the operating member formed by flange 131 to move proximally past trigger leg 193 without causing movement of latch 214 out of engagement with rail member 133. The force from tissue contact will cause portal sleeve 126 to move proximally against bias member 148 causing the operating member formed by flange 136 to move proximally past trigger leg 192 without causing movement of latch 182 out of engagement with rail member forward wall 142. Accordingly, during penetration of the anatomical cavity wall, the penetrating member is moved proximally from the penetrating member extended position, and the portal sleeve is moved proximally from the portal sleeve retracted position. Upon penetration into the anatomical cavity by the safety penetrating instrument 120, the penetrating member 130 will be moved distally toward the penetrating member extended position causing flange 131 to engage trigger leg 193 and pivot trigger 195 counterclockwise looking at FIG. 5 such that latch 214 is moved out of engagement with rail member rearward wall 137. Accordingly, retracting member 145 will cause penetrating member 130 to move proximally to the penetrating member retracted position. Upon introduction of the safety penetrating instrument 120 in the anatomical cavity, the portal sleeve 126 will be moved distally toward the portal sleeve retracted position causing flange 136 to engage trigger leg 192 and pivot trigger 186 counterclockwise looking at FIG. 5 to move latch 182 out of engagement with rail member forward wall 142. Movement of latch 182 out of engagement with the rail member forward wall causes the portal sleeve 126 to be moved further distally by extending member 150 to the portal sleeve extended position. Movement of the portal sleeve 126 to the portal sleeve extended position can be seen by the surgeon by noticing movement of the handle 160 toward a distal end of slot 159 and observation of the indicator strip 161. Movement of the penetrating member 130 to the penetrating member retracted position can be confirmed visually by noticing movement of handle 149 toward a proximal end of slot 147.

The distal bias for the portal sleeve toward the portal sleeve retracted position and the distal bias for the penetrating member toward the penetrating member extended position need only be great enough to produce slight longitudinal movement of the operating members past the triggers such that the force-to-penetrate can be minimized. By providing separate, independent trigger mechanisms for releasing the safety member to move to the safety member extended position and for releasing the penetrating member to move to the penetrating member retracted position, the safety and efficacy of safety penetrating instruments can be enhanced.

Figure 6:
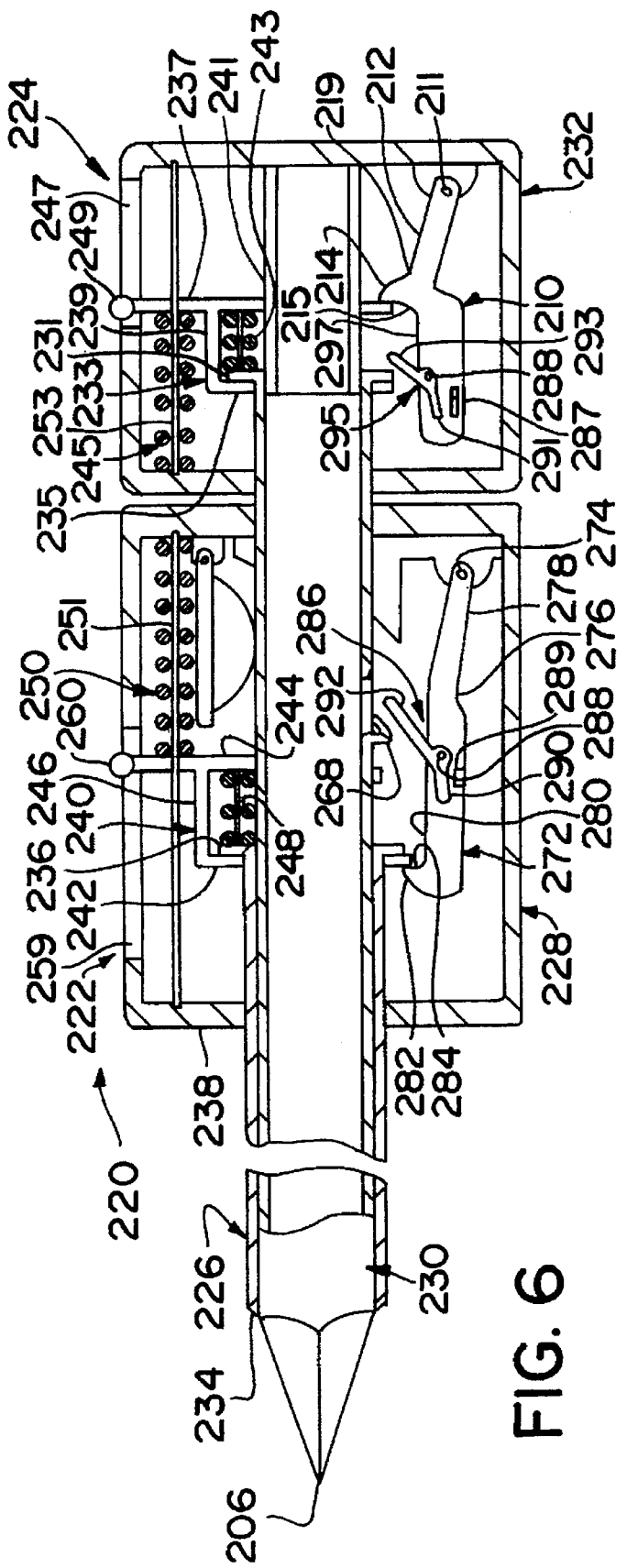
FIG. 6 is a broken side view, partly in section, of yet another safety penetrating instrument according to the present invention.

Another modification of the safety penetrating instrument 20 is shown in FIG. 6 with the primary difference being that distal movement of the penetrating member upon entering the anatomical cavity triggers automatic retraction of the penetrating member and simultaneous protrusion of the portal sleeve. Like safety penetrating instruments 20 and 120, the modified safety penetrating instrument 220 includes a portal unit 222 and a penetrating unit 224. The portal unit 222 includes a safety member, such as a cannula or portal sleeve 226, and a housing 228 mounting the proximal end of the portal sleeve 226. The penetrating unit 224 is shown coupled with the portal unit 222 and includes a penetrating member 230 disposed in portal sleeve 226 and a hub 232 mounting the proximal end of the penetrating member 230. The penetrating member 230 terminates distally in a distal end 205, shown with facets tapering distally to define a sharp tissue penetrating tip 206. In the extended position, the tapered portion of the penetrating member distal end 205 is aligned with the chamfered portal sleeve distal end 234 to provide a smooth distal profile.

A rail member 240, similar to rail member 40, is disposed within the housing 228 and has a generally U-shaped configuration with spaced, parallel forward and rearward walls 242 and 244, respectively, and a side wall 239 connecting the rail member forward and rearward walls 242 and 244. Portal sleeve 226 passes through aligned openings in the front wall 238 of the housing 228 and the rail member forward wall 242, terminating proximally in a transverse tab or flange 236 disposed between the rail member forward and rearward walls 242 and 244. A bias member 248 is connected between the flange 236 and the rail member rearward wall 244 to bias the penetrating member in a distal direction such that flange 236 is biased in abutment with rail member forward wall 242. Bias member 248 is shown as a helical coil spring disposed around a guide shaft; however, bias member 248 can include any other type of spring or other bias device as previously discussed for bias member 48. Rail member 240 differs somewhat from rail member 40 in that rearward wall 244 extends beyond side wall 246 toward an opening 259 formed in the side of the housing 228 to connect with a handle 260 movable along the opening 259. An extending member 250 in the form of a helical spring surrounding a guide rod 251 is held in compression between a rear wall of the housing 228 and the rail member rearward wall 244. It will be appreciated, however, that the extending member 250 can include various other types of springs or other bias devices as previously described.

A latch 272 has a proximal end rotatably mounted on a pin 274 secured to the rear wall of the housing 228 or a structure supported in the housing. A torsion spring (not shown) is coiled around the pin 274 and fixed to the latch 272 to bias the latch clockwise looking at FIG. 6. The latch proximal end includes an upwardly extending arm 278 that extends distally from the rear wall of the housing 228 at an angle and is joined at a bend 276 to an approximately horizontal distal extension 280. A latching protrusion or pawl 282 having a proximal latching surface 284 is formed at a distal end of the extension 280 and configured to engage the rail member forward wall 242 to permit proximal movement of the rail member 240 over the protrusion 282 while preventing distal movement when engaged. A trigger lever 286 is rotatably mounted on a pin 288 secured to the latch 272 proximally of protrusion 282. The trigger 286 is generally L-shaped with a leg 290 oriented parallel to the latch distal end and a leg 292 extending transversely at a slight angle toward the penetrating member 230. A nub 289 is carried on the latch distal extension 280 and positioned adjacent to leg 290 to prevent rotation of the trigger lever 286 counterclockwise looking at FIG. 6. A torsion spring is coiled around the pin 288 and fixed to the lever 286 to bias the lever against the nub 289 while permitting clockwise rotation.

Figure 7:
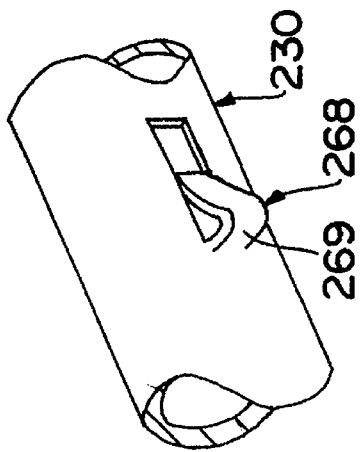
FIG. 7 is an enlarged perspective view of the protrusion carried by the penetrating member of the safety penetrating instrument of FIG. 6.

Penetrating member 230 includes a tab or prong 268 formed intermediate the penetrating member proximal and distal ends and distally spaced from trigger leg 292 when the penetrating member 230 is extended. The prong 268 can be formed from a tongue of material cut from the tubular body of the penetrating member 230, as shown in FIG. 7, or can be a separate member carried by the penetrating member and configured to present a distally facing abutment surface 269 to engage the trigger leg 292.

A rail member 233, similar to rail member 240, is disposed within the hub 232 and has a generally U-shaped configuration with spaced, parallel forward and rearward walls 235 and 237, respectively, and a side wall 239 connecting the rail member forward and rearward walls 235 and 237. The penetrating member 230 226 passes through aligned openings in the front wall of the hub 232 and the rail member forward wall 235, terminating proximally in a transverse tab or flange 231 disposed between the rail member forward and rearward walls 235 and 237. A bias member 243 is connected between the flange 231 and the rail member rearward wall 237 to bias the penetrating member in a distal direction such that flange 231 is biased in abutment with rail member forward wall 235. Bias member 243, like bias member 248, is shown as a helical coil spring disposed around a guide shaft; however, bias member 243 can include any other type of spring or other bias device as previously discussed for bias member 48. Rail member rearward wall 237 extends beyond side wall 239 toward an opening 247 formed in the side of the hub 232 to connect with a handle 249 movable along the opening 247. A retracting member 245 in the form of a helical spring surrounding a guide rod 253 is held in compression between the front wall of the hub 232 and the rail member rearward wall 235 to proximally bias the penetrating member 230 toward the retracted position.

A second latch 210, similar to latch 272, extends distally from the rear wall of the hub 232 to engage the rail member rearward wall 237 to prevent proximal movement thereof when locked. The latch 210 includes an upwardly angled arm 212 rotatably mounted on a pin 211 secured to the rear wall of the hub, and an approximately horizontal distal extension 297 joining the arm 212 at a bend 219. A latching protrusion or pawl 214 is formed at the proximal end of the distal extension 297 for engaging the rail member 233 to prevent proximal movement thereof during penetrating of an anatomical cavity wall. A trigger lever 295 is rotatably mounted on a pin 288 carried near the distal end of the latch 210 and is generally L-shaped, including a leg 291 extending parallel the distal extension 297 above a nub 287 and a leg 293 extending transversely and at a slight angle to be positioned proximally of the transverse flange 231 of the penetrating member 230 when the penetrating member 230 is extended and the flange 231 is biased against the forward wall 235 of the rail member 233.

In operation, the safety penetrating instrument 220 is provided with the penetrating member 230 in the retracted position and the portal sleeve 226 in the extended position so that the portal sleeve distal end 234 extends distally beyond the tip of the penetrating member 230. Handles 260 and 249 are used to extend the penetrating member 230 and to retract the portal sleeve 226 to the positions shown in FIG. 6, where they are locked in place by latches 210 and 272, respectively. Portal sleeve 226 and penetrating member 230 move together proximally during penetration of an anatomical cavity wall against the distal bias of springs 248 and 243 to maintain the alignment of their distal ends; however, it is distal movement of the penetrating member 230 upon penetrating into the anatomical cavity that ultimately triggers retraction of the penetrating member 230 and extension of the portal sleeve 226. More specifically, during penetration into the cavity wall, the penetrating member 230 moves proximally against the distal bias of spring 243 causing prong 268 formed in penetrating member 230 to bear against trigger lever 286 while the transverse flange 231 of the penetrating member 230 bears against trigger lever 295, causing both trigger levers to rotate clockwise looking at FIG. 8. Prong 268 and flange 231 thus pass over the trigger legs 292 and 293, respectively, which legs spring back to be disposed distally of the prong 268 and flange 231 during penetration. When the penetrating member 230 penetrates into the anatomical cavity, springs 243 and 248 urge the portal sleeve 226 and penetrating member 230 distally forward causing the prong 268 and transverse flange 231 of the penetrating member 230 to bear distally against trigger legs 292 and 293, respectively. The trigger levers 286 and 295 are thus rotated counterclockwise until legs 290 and 291 bear against nubs 290 and 297 and are stopped. The distal force exerted against the levers 286 and 295 creates a moment which rotates latches 272 and 210 away from the portal sleeve extending rail member 240 and the penetrating member retracting rail member 233. With latches 210 and 272 released, extending member 250 operates to move portal sleeve 226 further in a distal direction to the extended position, and retracting member 245 operates to move penetrating member 230 from the extended position to the retracted position. With the tip 206 of the penetrating member 230 safely protected within the portal sleeve 226, the penetrating unit 224 can be removed from the portal unit 222 leaving the portal sleeve 226 in place for performing various surgical and diagnostic procedures through the lumen thereof.

It will be appreciated that the safety penetrating instrument 220 provides a redundant safety mechanism by at once triggering retraction of the penetrating member and protrusion of the portal sleeve to position the tip of the penetrating member in a protected state. Since either mechanism would suffice to protect the penetrating member tip, the provision of both mechanisms provides an additional safeguard against malfunction. Additionally, by locating the extending mechanism within the housing and the retracting mechanism within the hub, it is possible to reduce the size of the hub and, therefore, to improve the handling characteristics and reduce the overall size of the safety penetrating instrument while maintaining a suitable amount of relative movement between the penetrating member and the portal sleeve.

Figure 8:
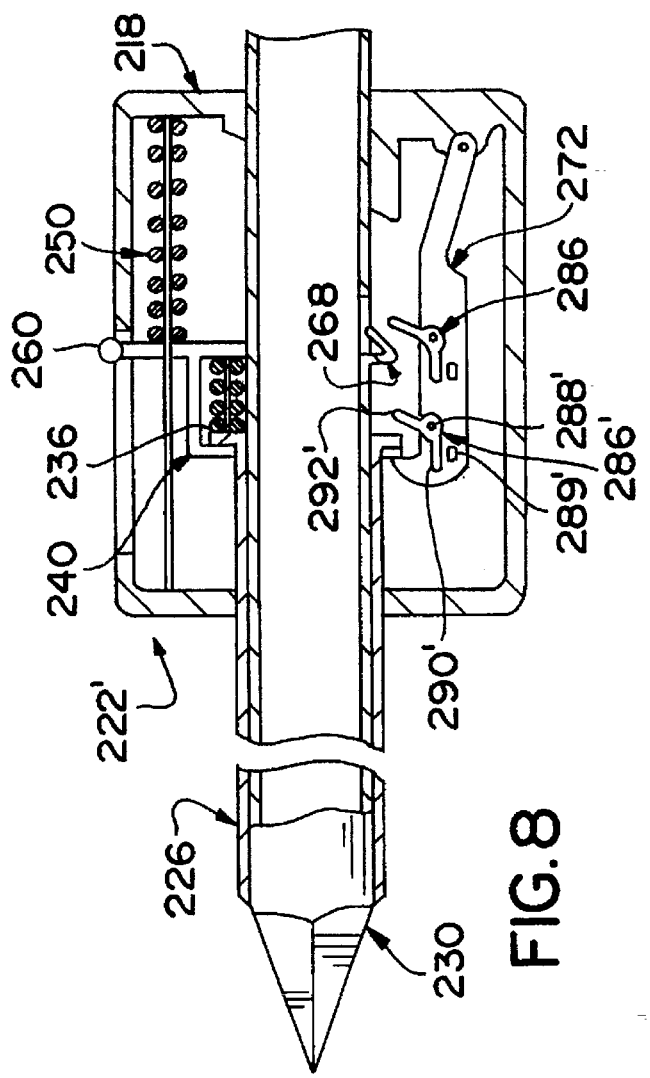
FIG. 8 is a broken side view, partly in section, of still another safety penetrating instrument according to the present invention.

The portal unit 222' of still another modification of the safety penetrating instrument of the present invention is illustrated in FIG. 8; it being understood that a cooperating penetrating unit can be configured as shown in FIG. 6 or in any other manner to mate with the portal unit and to retract the penetrating member in response to movement of one or both of the penetrating member and portal sleeve of the safety penetrating instrument. The modified safety penetrating instrument is similar to the safety penetrating instrument 220 shown in FIG. 6, but has two trigger levers 286 and 286' carried on the latch 272 holding the portal sleeve extending rail member 240. The trigger lever 286' is identical to trigger lever 286 previously described, and is rotatably mounted on a pin 288' secured to the latch 272 distally of trigger lever 286 to engage the portal sleeve flange 236. The trigger lever 286' is generally L-shaped and has one leg 290' normally extending parallel the latch distal end and a leg 292' normally extending transversely at a slight angle to be positioned proximally of the portal sleeve flange 236.

It will be appreciated that by carrying two trigger levers on the latch holding the portal sleeve extending rail member, extension of the portal sleeve will be actuated in response to distal movement of either or both of the portal sleeve and penetrating member upon penetrating into an anatomical cavity. Multiple triggering ensures extension of the portal sleeve even if one of the members fails to move. When coupled with penetrating unit 214, the modified safety penetrating unit is also responsive to distal movement of the penetrating member to trigger retraction of the penetrating member into the hub, further increasing the overall safety of the penetrating instrument.

From the above, it will be appreciated that the safety penetrating instrument of the present invention provides substantially simultaneous triggered retraction of a penetrating member and triggered protrusion of a safety member to provide two modes of protecting the tip of the penetrating member upon penetration of the safety penetrating instrument into an anatomical cavity. By "safety member" is meant any structure movable relative to the penetrating member to protrude distally beyond the penetrating member tip to prevent contact between the tip and anatomical tissue or organs. Hence, cannulas, such as portal sleeves, catheters, and needles and other tubular members, such as safety shields, that surround the penetrating member can function as safety members when they extend beyond a penetrating member tip. Similarly, probes that fit within or partly within and around the penetrating member and extend through openings formed in the penetrating member can also function as safety members when they extend beyond the penetrating member tip.

Figure 10:
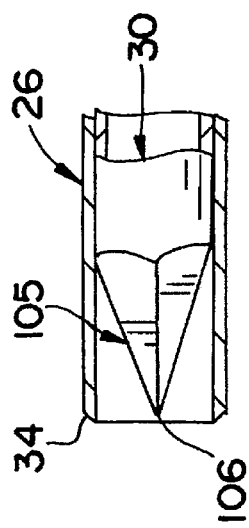
FIG. 10 is a side view, partly in section, of another alternative distal end alignment for a safety penetrating instrument according to the present invention.
Figure 9:
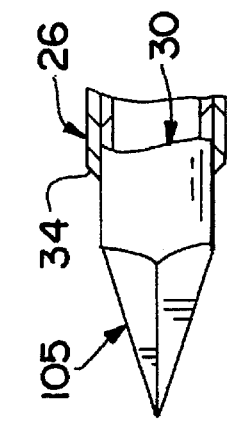
FIG. 9 is a side view, partly in section, of an alternative distal end alignment for a safety penetrating instrument according to the present invention.

The retracting and extending functions of the safety penetrating instrument of the present invention can be triggered individually or together by movement of one or both of the penetrating member and the safety member. Either one or both of the penetrating member and safety member can be mounted on bias members, such as helical coil springs, to be distally biased while allowing proximal movement during penetration of the anatomical cavity wall. If both members are mounted on bias members, they can move together during penetration of the anatomical cavity wall and the alignment of their distal ends will be maintained as shown in FIG. 6 to provide a smooth profile during penetration. If, however, one of the members is fixed to the housing or hub or otherwise locked in place during penetration through the cavity wall, the other distally biased member can be spaced distally from the distal end of the fixed member prior to penetration so that upon contacting the anatomical tissue the biased member will move proximally into alignment with the distal end of the fixed member. For example, if a penetrating member 30 is distally biased and a portal sleeve 26 is fixed, the penetrating member distal end 105 can be spaced distally from the portal sleeve distal end 34 as shown in FIG. 9. Similarly, if the portal sleeve 26 is distally biased and the penetrating member 30 is fixed, the portal sleeve distal end 34 can be spaced distally of the penetrating member 30 to cover the tip 106 as shown in FIG. 10.

The components of the safety penetrating instruments of the present invention can be made of any suitable, medical grade materials to permit sterilization for reuse or for single patient use. The components can be made of multiple parts of various configurations and materials to reduce cost. The portal unit can have various valves, stop cocks and seals in the housing to control fluid flow therethrough and various adapters to adjust to the size of the instruments inserted through the portal unit. The safety member can be part of the portal unit or the penetrating unit such that the safety member can remain in place in the anatomical cavity upon withdrawal of the penetrating unit or can be withdrawn with the penetrating unit. The rail members can have various configurations to engage the latches and be released by the triggers and can have configurations to serve as a stop or abutment for the operating members.

Where the penetrating member includes a needle, the slots and handles can be eliminated, and the hub and/or housing can have a transparent section with a colored ball movable therein to provide an indication confirming penetration into the anatomical cavity. Where a handle and slot are provided for the safety member and/or the penetrating member, it will be appreciated that the handles can be utilized to manually move the safety member proximally from and distally toward the safety member retracted position and/or the penetrating member proximally from and distally toward the penetrating member extended position.

The locking and releasing mechanisms require only a latch for locking the safety member in the safety member retracted position and the penetrating member in the penetrating member extended position and triggers for releasing the latch in response to distal movement of one or more operating members. When separate latches are used for locking the penetrating member and safety member prior to use, one or both of the members can be locked by selectively operating the appropriate handles together or on an individual basis. For example, if the handle connecting the penetrating member is operated to lock the penetrating member in the penetrating member extended position, the handle connecting the safety member may or may not be operated to lock the safety member in the safety member retracted position. If the safety member handle is not operated, the safety member will not be triggered to protrude and the safety penetrating instrument will function as a retractable safety penetrating instrument only. It will be appreciated that various mechanisms can be employed to produce the locking and releasing functions such as, for example, multiple movably or pivotally mounted cams or pawls. It will be appreciated that the locking and releasing mechanisms can be arranged in the housing and/or the hub or within the penetrating member in many various ways to minimize the length of the housing and/or the hub and, therefore, the overall length of the safety penetrating instruments. Some of the locking and releasing mechanisms that can be used in the safety penetrating instruments of the present invention are disclosed in applicant's pending applications Ser. No. 07/800,507, filed Nov. 27, 1991, Ser. No. 07/805,506, filed Dec. 6, 1991, Ser. No. 07/808,325, filed Dec. 16, 1991, Ser. No. 07/848,838, filed Mar. 10, 1992, Ser. No. 07/868,566 and Ser. No. 07/868,578, filed Apr. 15, 1992, Ser. No. 07/929,338, filed Aug. 14, 1992, Ser. No. 07/845,177, filed Sep. 15, 1992, Ser. No. 07/945,177, filed Sep. 15, 1992, Ser. No. 08/079,586, filed Jun. 22, 1993, Ser. No. 08/195,512, filed Feb. 14, 1994, Ser. No. 08/196,029, filed Feb. 14, 1994, Ser. No. 08/196,027, filed Feb. 14, 1994, Ser. No. 08/195,178, filed Feb. 14, 1994, Ser. No. 08/237,734, filed May 4, 1994, Ser. No. 08/247,205, filed May 20, 1994, Ser. No. 08/254,007, filed Jun. 3, 1994 and Ser. No. 08/260,439, filed Jun. 15, 1994, the disclosures of which are incorporated herein by reference.

The features of the various embodiments described above can be combined in any manner desired dependent upon the requirements and complexity of the safety penetrating instrument. Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A safety penetrating instrument for establishing a portal in a wall of an anatomical cavity comprising a hub;

a penetrating member mounted by said hub and movable relative thereto between a penetrating member extended position and a penetrating member retracted position, said penetrating member having a sharp distal end for penetrating the anatomical cavity wall;

a safety member movable relative to said hub between a safety member retracted position exposing said sharp distal end of said penetrating member when said penetrating member is in said penetrating member extended position and a safety member extended position protecting said sharp distal end of said penetrating member;

retracting means for moving said penetrating member proximally relative to said hub from said penetrating member extended position to said penetrating member retracted position;

extending means for moving said safety member distally relative to said hub from said safety member retracted position to said safety member extended position;

locking means for locking said penetrating member in said penetrating member extended position and said safety member in said safety member retracted position to prevent distal movement of said safety member relative to said hub beyond said safety member retracted position; and releasing means responsive to entry of said safety penetrating instrument into the anatomical cavity for triggering release of said locking means to permit said retracting means to move said penetrating member proximally relative to said hub from said penetrating member extended position to said penetrating member retracted position and to permit said extending means to move said safety member distally relative to said hub from said safety member retracted position to said safety member extended position to protect said sharp distal end of said penetrating member.

2. A safety penetrating instrument as recited in claim 1 wherein said penetrating member includes a proximal end and said safety member includes a proximal end and further comprising a housing mounting said proximal end of said safety member and wherein said hub mounts said proximal end of said penetrating member.

3. A safety penetrating instrument as recited in claim 1 wherein said releasing means is responsive to entry of said safety member into the anatomical cavity.

4. A safety penetrating instrument as recited in claim 3 and further comprising bias means for biasing said safety member distally relative to said hub while permitting a predetermined amount of proximal movement thereof relative to said hub during penetration of the anatomical cavity wall and wherein said releasing means is responsive to distal movement of said safety member relative to said hub caused by said bias means upon entry of said safety member into the anatomical cavity.

5. A safety penetrating instrument as recited in claim 1 wherein said releasing means is responsive to entry of said penetrating member into the anatomical cavity.

6. A safety penetrating instrument as recited in claim 5 and further comprising bias means for biasing said penetrating member distally relative to said hub while permitting a predetermined amount of proximal movement thereof relative to said hub during penetration of the anatomical cavity wall and wherein said releasing means is responsive to distal movement of said penetrating member relative to said hub caused by said bias means upon entry of said penetrating member into the anatomical cavity.

7. A safety penetrating instrument as recited in claim 6 wherein said safety member terminates proximally in a flange, said penetrating member terminates proximally in a flange, and said locking means includes a first latch for engaging said penetrating member flange and a second latch for engaging said safety member flange.

8. A safety penetrating instrument as recited in claim 7 and further comprising a protrusion carried by said penetrating member intermediate said penetrating member proximal and distal ends, wherein said releasing means includes a first trigger lever mounted on said first latch proximal said penetrating member flange and a second trigger lever mounted on said second latch proximal said protrusion.

9. A safety penetrating instrument as recited in claim 1 wherein said releasing means is responsive to entry of said penetrating member and said safety member into the anatomical cavity.

10. A safety penetrating instrument as recited in claim 9 and further comprising bias means for biasing said safety member and said penetrating member distally relative to said hub while permitting a predetermined amount of proximal movement of each member relative to said hub during penetration of the anatomical cavity wall and wherein said releasing means is responsive to distal movement of said safety member and said penetrating member caused by said bias means upon entry of said at least one of said safety member and said penetrating member into the anatomical cavity.

11. A safety penetrating instrument as recited in claim 10 wherein said safety member terminates proximally in a flange, said penetrating member terminates proximally in a flange, and said locking means includes a first latch for engaging said penetrating member flange and a second latch for engaging said safety member flange.

12. A safety penetrating instrument as recited in claim 11 and further comprising a protrusion carried by said penetrating member intermediate said penetrating member proximal and distal ends, wherein said releasing means includes a first trigger lever mounted on said first latch proximal said penetrating member flange, a second trigger lever mounted on said second latch proximal said protrusion and a third trigger lever mounted on said second latch proximal said portal sleeve flange.

13. A safety penetrating instrument for penetrating anatomical tissue to gain access to an anatomical cavity comprising a hub;

a penetrating member mounted by said hub and movable relative thereto between a penetrating member extended position and a penetrating member retracted position, said penetrating member having a sharp distal end for penetrating anatomical tissue;

a safety member having a distal end and being movable relative to said hub between a safety member extended position where said safety member distal end is disposed distally of said sharp penetrating member distal end and a safety member retracted position where said safety member distal end is disposed proximally of said penetrating member distal end;

extending means for moving said safety member distally relative to said hub from said safety member retracted position to said safety member extended position;

safety member bias means for biasing said safety member distally relative to said hub in said safety member retracted position and for permitting said safety member to move proximally relative to said hub from said safety member retracted position during penetration of the anatomical tissue and distally relative to said hub toward said safety member retracted position upon introduction of said safety penetrating instrument in the anatomical cavity;

retracting means for moving said penetrating member proximally relative to said hub from said penetrating member extended position where said sharp penetrating member distal end is disposed distally of said safety member distal end and said penetrating member retracted position where said sharp penetrating member distal end is disposed proximally of said safety member distal end;

locking means for locking said safety member in said safety member retracted position to prevent distal movement of said safety member relative to said hub beyond said safety member retracted position while permitting proximal movement of said safety member relative to said hub from said safety member retracted position during penetration of the anatomical tissue and for locking said penetrating member in said penetrating member extended position during penetration of the anatomical tissue; and releasing means responsive to movement of said safety member distally toward said safety member retracted position upon introduction of said safety penetrating instrument in the anatomical cavity for triggering release of said locking means to permit said extending means to move said safety member distally relative to said hub from said safety member retracted position to said safety member extended position and to permit said retracting means to move said penetrating member proximally relative to said hub from said penetrating member extended position to said penetrating member retracted position.

14. A safety penetrating instrument as recited in claim 13 wherein said locking means includes safety member locking means for preventing movement of said safety member to said safety member extended position and penetrating member locking means for preventing movement of said penetrating member to said penetrating member retracted position during penetration of the anatomical tissue.

15. A safety penetrating instrument as recited in claim 14 wherein said releasing means includes safety member trigger means for triggering release of said safety member locking means and penetrating member trigger means for triggering release of said penetrating member locking means.

16. A safety penetrating instrument as recited in claim 15 and further including operating means coupled with said safety member and movable therewith for engaging said safety member trigger means and said penetrating member trigger means to trigger release of said safety member locking means and said penetrating member locking means in response to movement of said safety member distally toward said safety member retracted position.

17. A safety penetrating instrument as recited in claim 16 wherein said safety member includes a proximal end and further comprising a housing mounting said proximal end of said safety member and wherein said operating means is disposed in said housing.

18. A safety penetrating instrument as recited in claim 17 wherein said extending means is disposed in said housing and includes a pair of legs pivotally connected to one another, one of said legs being secured to said housing and the other of said legs being coupled with said safety member, said other of said legs being biased toward said one leg to move said safety member distally to said safety member extended position.

19. A safety penetrating instrument as recited in claim 17 wherein said penetrating member locking means is disposed in said penetrating member.

20. A safety penetrating instrument for penetrating anatomical tissue to gain access to an anatomical cavity comprising a penetrating member having a distal end for penetrating anatomical tissue;

a safety member having a distal end and being movable relative to said penetrating member from a safety member extended position where said safety member distal end is disposed distally of said sharp penetrating member distal end to a safety member retracted position where said safety member distal end is disposed proximally of said sharp penetrating member distal end;

extending means for moving said safety member to said safety member extended position and for permitting movement of said safety member to said safety member retracted position;

retracting means for moving said penetrating member proximally relative to said safety member from a penetrating member extended position where said sharp penetrating member distal end is disposed distally of said safety member distal end with said safety member in said safety member retracted position and a penetrating member retracted position where said sharp penetrating member distal end is disposed proximally of said safety member distal end with said safety member in said safety member retracted position;

safety member locking means for locking said safety member in said safety member retracted position to prevent movement of said safety member to said safety member extended position during penetration of the anatomical tissue;

penetrating member locking means for locking said penetrating member in said penetrating member extended position during penetration of the anatomical tissue; and operating means movable proximally during penetration of the anatomical tissue by said safety penetrating instrument and movable distally upon introduction of said safety penetrating instrument in the anatomical cavity for triggering release of said safety member locking means and said penetrating member locking means to permit said extending means to move said safety member distally to said safety member extended position and said retracting means to move said penetrating member proximally to said penetrating member retracted position.

21. A safety penetrating instrument as recited in claim 20 and further including means for manually moving said safety member from said safety member extended position to said safety member retracted position.

22. A safety penetrating instrument as recited in claim 21 and further including means for manually moving said penetrating member from said penetrating member retracted position to said penetrating member extended position.

23. A safety penetrating instrument as recited in claim 20 wherein said operating means is coupled with said safety member and said safety member is movable with said operating means proximally from said safety member retracted position during penetration of the anatomical tissue by said retractable penetrating instrument and distally toward said safety member retracted position upon introduction of said safety penetrating instrument in the anatomical cavity.

24. A safety penetrating instrument as recited in claim 23 and further including trigger means for being engaged by said operating means when said operating means is moved distally upon introduction of said safety penetrating instrument in the anatomical cavity.

25. A safety penetrating instrument as recited in claim 24 wherein said trigger means includes a safety member trigger for releasing said safety member locking means and a penetrating member trigger for releasing said penetrating member locking means.

26. A safety penetrating instrument as recited in claim 20 wherein said penetrating member includes an end part and a distal part mounted for telescoping, sliding movement relative to said end part and said retracting means biases said distal part proximally relative to said end part to said penetrating member retracted position.

27. A safety penetrating instrument as recited in claim 26 wherein said retracting means is disposed in said distal part.

28. A safety penetrating instrument as recited in claim 27 wherein said penetrating member locking means is disposed in said end part to engage said distal part to prevent proximal movement of said distal part relative to said end part.

29. A safety penetrating instrument for penetrating anatomical tissue to gain access to an anatomical cavity comprising a portal sleeve having a distal end for positioning in the anatomical cavity, a proximal end and a lumen extending between said distal and proximal portal sleeve ends;

a penetrating member disposed in said lumen of said portal sleeve and having a distal end for penetrating anatomical tissue and a proximal end;

extending means for biasing said portal sleeve distally to a portal sleeve extended position where said portal sleeve distal end is disposed distally of said sharp penetrating member distal end and for permitting said portal sleeve to move proximally to a portal sleeve retracted position where said portal sleeve distal end is disposed proximally of said sharp penetrating member distal end;

portal sleeve bias means for biasing said portal sleeve distally in said portal sleeve retracted position and for permitting said portal sleeve to move proximally from said portal sleeve retracted position during penetration of the anatomical tissue and distally toward said portal sleeve retracted position upon introduction of said safety penetrating instrument in the anatomical cavity;

retracting means for biasing said penetrating member proximally to a penetrating member retracted position where said sharp penetrating member distal end is disposed proximally of said portal sleeve distal end with said portal sleeve in said portal sleeve retracted position and for permitting said penetrating member to move distally to a penetrating member extended position where said sharp penetrating member distal end is disposed distally of said portal sleeve distal end with said portal sleeve in said portal sleeve retracted position;

penetrating member bias means for biasing said penetrating member distally in said penetrating member extended position and for permitting said penetrating member to move proximally from said penetrating member extended position during penetration of the anatomical tissue and distally toward said penetrating member extended position upon introduction of said safety penetrating instrument in the anatomical cavity;

portal sleeve locking means for locking said portal sleeve in said portal sleeve retracted position to prevent movement of said portal sleeve to said portal sleeve extended position during penetration of the anatomical tissue;

penetrating member locking means for locking said penetrating member in said penetrating member extended position to prevent movement of said penetrating member to said penetrating member retracted position during penetration of the anatomical tissue;

portal sleeve releasing means responsive to movement of said portal sleeve distally toward said portal sleeve retracted position for triggering release of said portal sleeve locking means to permit said extending means to move said portal sleeve to said portal sleeve extended position; and penetrating member releasing means responsive to movement of said penetrating member distally toward said penetrating member extended position for triggering release of said penetrating member locking means to permit said retracting means to move said penetrating member to said penetrating member retracted position.

30. A safety penetrating instrument as recited in claim 29 and further including a housing mounting said portal sleeve proximal end and a hub mounting said penetrating member proximal end.

31. A safety penetrating instrument as recited in claim 30 wherein said portal sleeve locking means and said portal sleeve releasing means are disposed in said housing and said penetrating member locking means and said penetrating member releasing means are disposed in said hub.

32. A safety penetrating instrument as recited in claim 31 wherein said portal sleeve releasing means includes a trigger in said housing for releasing said portal sleeve locking means and said penetrating member releasing means includes a trigger in said hub for releasing said penetrating member locking means.

33. A method of forming a portal in the wall of an anatomical cavity comprising the steps of moving a penetrating member of a safety penetrating instrument distally relative to a hub of the safety penetrating instrument from a penetrating member retracted position to a penetrating member extended position;

moving a safety member of the safety penetrating instrument proximally relative to the hub from a safety member extended position to a safety member retracted position;

mechanically locking the penetrating member in the penetrating member extended position and the safety member in the safety member retracted position;

penetrating the anatomical cavity wall with the penetrating member locked in the penetrating member extended position and the safety member locked in the safety member retracted position;

mechanically unlocking the penetrating member and the safety member when the safety penetrating instrument enters the anatomical cavity;

moving the penetrating member proximally relative to the hub from the penetrating member extended position to the penetrating member retracted position; and moving the safety member distally relative to the hub from the safety member retracted position to the safety member extended position.

34. A method as recited in claim 33 and further comprising, after said locking step and prior to said penetrating step, biasing at least one of the penetrating member and the safety member in a distal direction relative to the hub while permitting a predetermined amount of proximal movement relative to the hub during said penetrating step.

35. A method as recited in claim 34 wherein unlocking of the penetrating member and the safety member occurs upon entry of the safety member into the anatomical cavity.

36. A method as recited in claim 34 wherein unlocking of the penetrating member and the safety member occurs upon entry of the penetrating member into the anatomical cavity.

37. A method as recited in claim 34 wherein unlocking of the penetrating member and the safety member occurs upon entry of the penetrating member and the safety member into the anatomical cavity.

* * * * *